United States Patent [19]
Amos et al.

[11] 4,130,824
[45] Dec. 19, 1978

[54] RECORDING ANALYZER FOR ELECTROPHORETIC SAMPLES

[75] Inventors: Lynn G. Amos, Corning; Howard F. Banks, Horseheads, both of N.Y.; Robert T. Buck, Raleigh, N.C.; William R. Eppes, Painted Post, N.Y.

[73] Assignee: Corning Glass Works, Corning, N.Y.

[21] Appl. No.: 799,942

[22] Filed: May 24, 1977

[51] Int. Cl.² .............................................. G01D 5/26
[52] U.S. Cl. .............................. 346/33 A; 346/33 B; 356/344
[58] Field of Search ................. 346/33 A, 29, 139 B; 364/498; 356/105, 203, 201; 204/299 R

[56] References Cited

U.S. PATENT DOCUMENTS

| | | | |
|---|---|---|---|
| 3,096,137 | 7/1963 | Silard | 346/33 A X |
| 3,614,241 | 10/1971 | Sanford | 356/203 X |
| 3,706,877 | 12/1972 | Clifford | 346/33 A X |
| 3,965,477 | 6/1976 | Hambleton | 346/33 A |

Primary Examiner—Joseph W. Hartary
Attorney, Agent, or Firm—Walter S. Zebrowski; Clarence R. Patty, Jr.; Richard E. Kurtz

[57] ABSTRACT

A recorder pen is mounted on the sample scanning stage of an electrophoretic sample analyzer. Movement of the stage scans the sample optically while, at the same time, the recorder pen produces an analog record of the optical analysis. A sample holder is mounted in the stage for detented movement in the direction orthogonal to the scanning motion of the sample stage. The sample holder can be moved to one of several detented positions so that different tracks of the samples are scanned.

11 Claims, 8 Drawing Figures

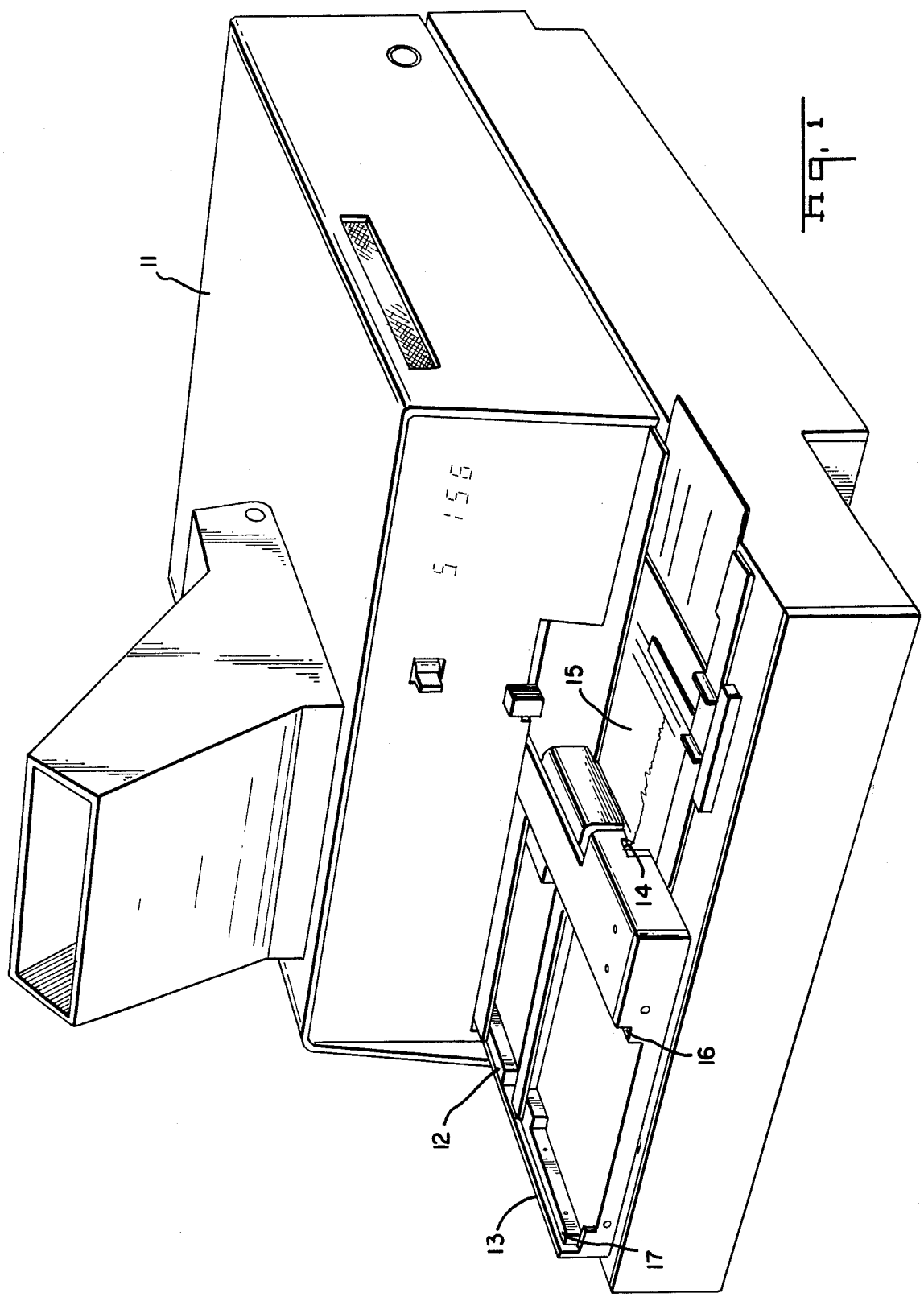

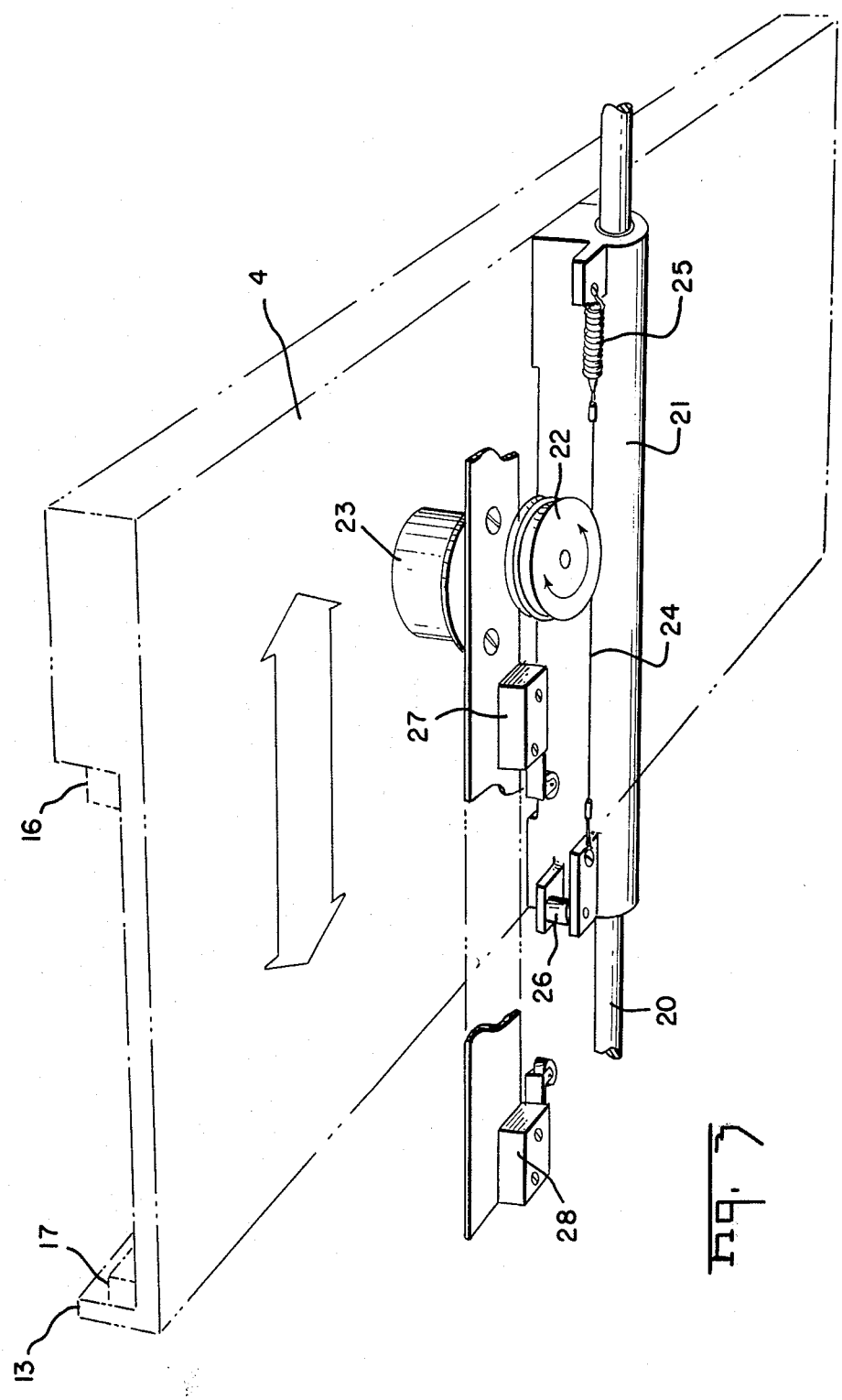

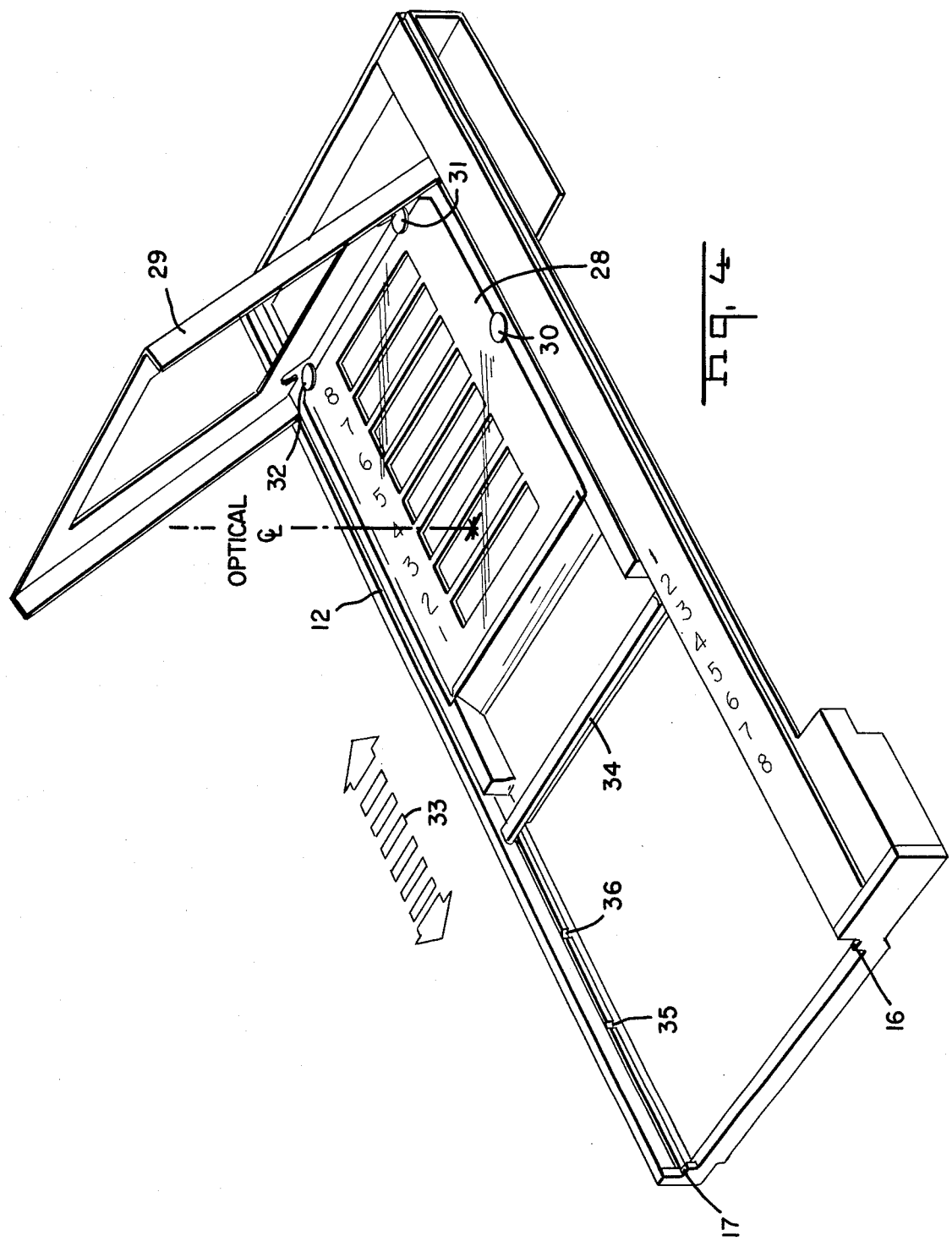

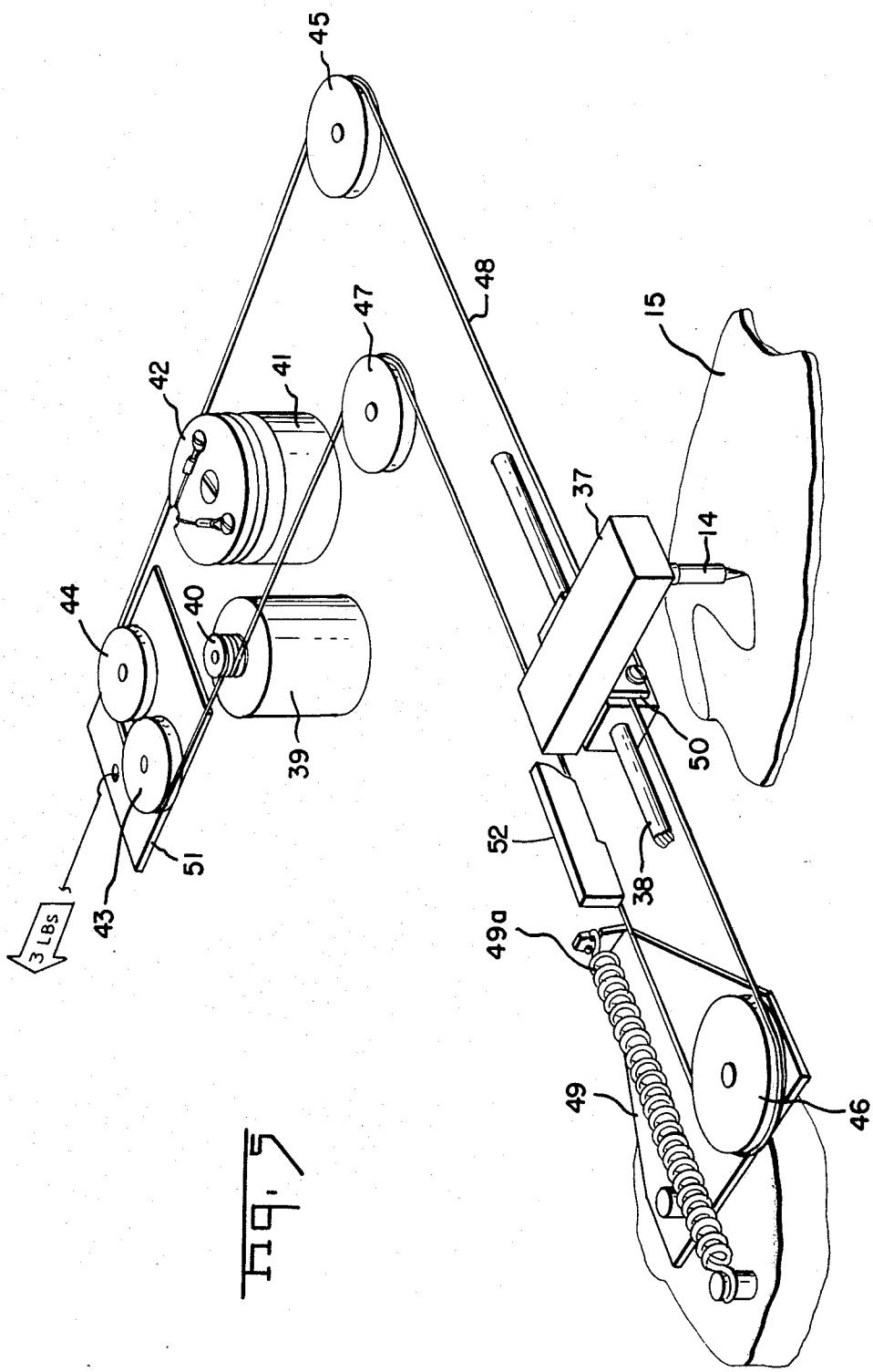

RECORDING ANALYZER FOR ELECTROPHORETIC SAMPLES

BACKGROUND OF THE INVENTION

This invention relates to an automatic recording fluorometer/densitometer.

Electrophoresis is a clinical procedure based on the phenomenon that charged molecules diffuse through a gel sample in response to an applied voltage.

U.S. Pat. Nos. 3,479,265 and 3,635,808 disclose thin film agarose sample plates which can be used as the electrophoretic medium. The thin film samples of these patents are particularly convenient for handling and storage.

These samples are analyzed by fluorometric or densitometric optical detection. One instrument for automatically making analyses of this type is described in U.S. Pat. No. 3,706,877.

A recorder which produces an analog record of the optical analysis is shown in U.S. Pat. No. 3,750,187 Keefer.

Instruments which optically or otherwise scan samples and produce an analog trace as an output have traditionally utilized one mechanism to transport the sample past the detector and another, generally a chart recorder or X, Y, plotter, to record the trace.

In using sample analyzers, it is necessary to visually align the sample plate with the scanning optics. Often, clinical procedure requires that the sample be scanned along several sample tracks. This visual alignment is time-consuming and subject to error.

RELATED CASES

Application Ser. No. 800,004, Adrion et al. filed concurrently herewith, shows the detection optics for the present invention. The disclosure of that application is incorporated herein by reference.

SUMMARY OF THE INVENTION

A simplified, reliable sample scanning mechanism and analog recorder are provided in accordance with this invention.

In accordance with this invention, the analog trace produced by the recorder is of the same length as the sample scan and the same movable state is used in the scanning and in the recording. As the stage is moved with respect to the detection optics, a recorder pen on the stage simultaneously is driven orthogonally to the scanning movement to produce a record of the characteristics in the scanning track along the sample. This arrangement greatly simplifies the mechanical operations of scanning and recording.

In accordance with another aspect of the invention, a sample holder is slidably mounted in the stage. The operator inserts a sample into the holder and then slides the holder into the case where it is aligned with the detection optics. Detents on the sample holder index the sample to different positions so that the sample can be scanned along different tracks. Locating pins and a hold-down cover align the sample with the detection optics, thereby eliminating the requirement for visual alignment. The invention reduces operator intervention and error.

A pen recorder includes a servomotor which is driven by the output of the detection optics. The pen transport mechanism includes a series of pulleys connected to the servomotor with no intervening gear train. At the "home" scanning position, the pen is lifted out of engagement with the record by a lifting cam. This arrangement provides a cost improvement and the pen recorder particularly meets the requirement for an electrophoretic sample analyzer.

The foregoing and other objects, features and advantages of the invention will be better understood from the following more detailed description and appended claims.

DESCRIPTION OF THE DRAWINGS

FIG. 1 is a perspective view of the analyzer of this invention;

FIG. 3 is a view of the bottom of the sample stage showing its drive mechanism;

FIG. 4 shows the sample holder;

FIG. 5 shows the pen drive mechanism; and

DESCRIPTION OF THE PREFERRED EMBODIMENT

Figure 2A:
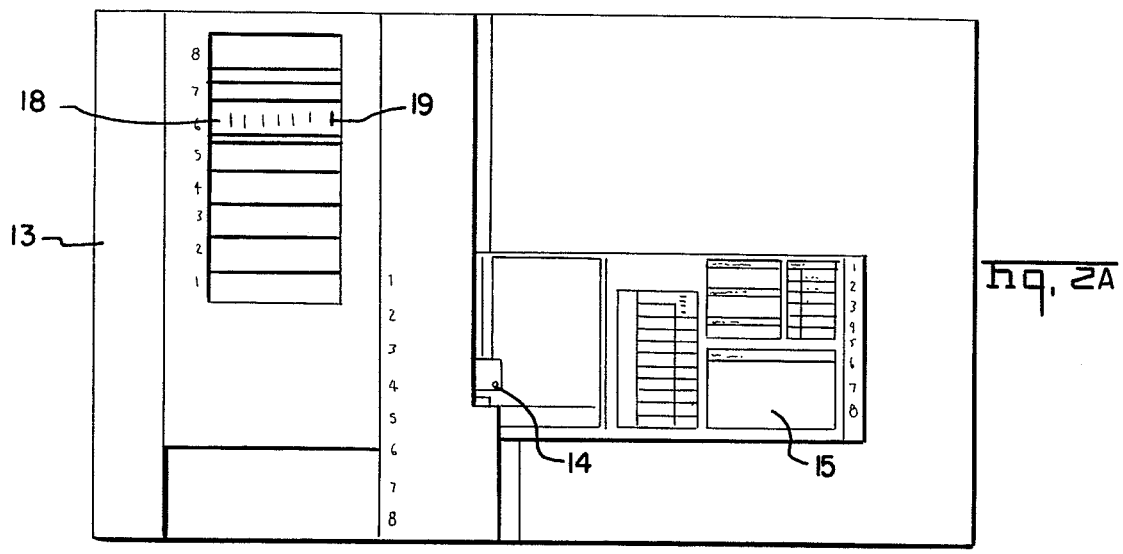
FIGS. 2A-2C depict the operation of the scanning stage as an analog trace is recorded.

The instrument of this invention includes a case 11 which encloses fluorometric and densitometric sources and optics. For automatic recording, the sample is inserted in the sample holder 12. The sample holder slides into the case between the light sources and the detection optics. The sample stage 13 moves in a horizontal direction to scan the light across the film. Concurrently, a recording pen 14 moves across the chart 15. A light detector measures light intensity from the sample, and the recording system responds to the output of the detector to move the recording pen 14 orthogonally to the scanning motion. This records the intensity of fluorescent light stimulated in fluorescent samples or transmitted light from densitometric samples.

The pen 14 is moved along chart 15 by the same movement which scans the sample across the source. This produces a record of the fluorescence or absorption characteristics across the sample. The record has the same length as the length of the track on the sample which is scanned.

Sample holder 12 slides along tracks 16 and 17 in the sample stage. The sample is placed in the holder and then the holder 12 is moved with respect to the sample stage in a direction orthogonal to the movement of the sample stage. This moves the sample holder into the case 11 into proximity with the sources and detection optics. It is shown in this position in FIG. 1 and FIGS. 2A-2C.

Figure 2B:
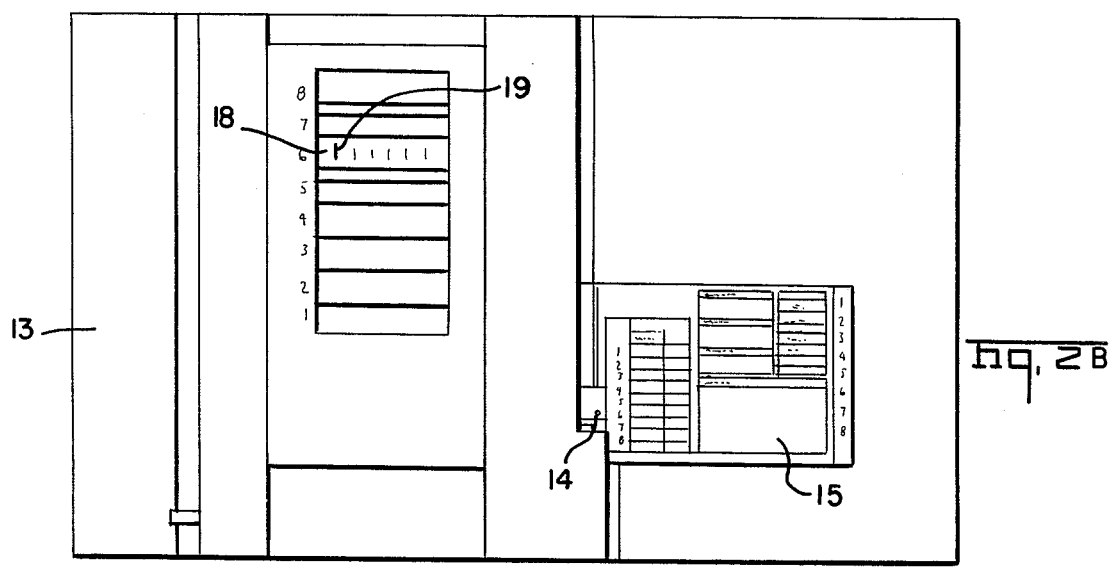
Figure 2C:
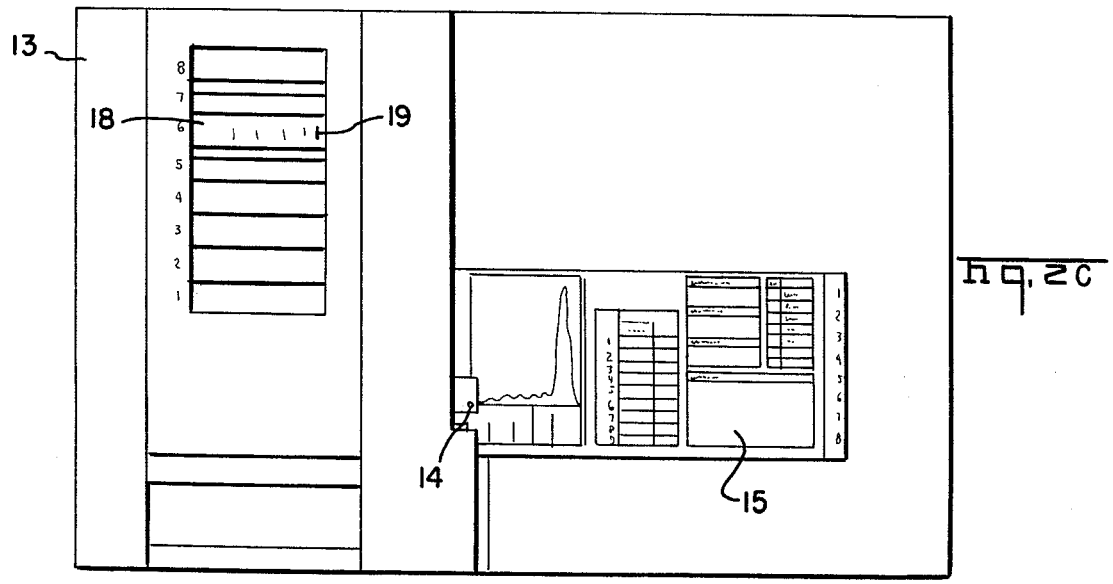

FIGS. 2A-2C depict the left to right and right to left scanning motion of the scanning stage 13. FIGS. 2A-2C show the sample 18 inside the case. The detection optics have an optical center line 19.

FIG. 2A shows the sample stage 13 and the recorder pen 14 in the "home" position. The optical center line 19 is at the right hand side of the sample 18. When the scan cycle is begun, the scanning stage 13 travels from left to right at a uniform rate. The sample 18 passes between the detector and the source which are aligned with the optical center line 19. During this left to right motion, the pen 14 draws a base line on the chart 15. At the end of this travel, a limit switch is actuated, and the direction of movement of the sample stage 13 is reversed. FIG. 2B illustrates the position of the stage 13 at this time. The optical center line is at the left hand edge of the track 6 on the sample.

The stage 13 now travels from right to left. As the sample 18 passes over the detector, it produces an output which drives the recorder pen 14 orthogonally to the direction of movement of the scanning stage. Pen 14 responds to the detector output generated by the varying radiation or density of the sample. A record is drawn on the chart as shown in FIG. 2C. Right to left travel is limited by actuation of a limit switch. Also, the pen cartridge moves to its home position below the baseline, contacting a lift cam during its travel which lifts the pen. The lifting facilitates insertion and withdrawal of the chart 15 without marking it and also prevents the pen 14 from weeping onto the surface of the chart.

As shown in FIG. 2C, the pen has drawn an analog record of the fluorescence or absorption characteristics of the sample. The length of the record is the same as the length of the track along sample 18 which has been scanned.

The sample transport mechanism for linearly moving the sample stage 13 is shown in FIG. 3. A way rod 20 is affixed at either end to the chassis (not shown) which is mounted in the case 11. A carrier 21 is affixed to the bottom of the sample stage 13. It slides along the way rod 20.

A pulley 22 is driven by a motor 23. Cable 24 is affixed at both ends to the carrier 21 with the spring 25 supplying tension. This tension provides the required friction between pulley 22 and cable 24 so that slipping will not occur under normal conditions.

Upon initiation of the scanning cycle, synchronous motor 23 is energized to rotate the pulley 22 counterclockwise. The motor continues to run, pulling the carrier 21 and the sample stage 13 along the way rod 20. When roller 26 depresses the actuator of the right limit switch 27, the rotation of drive motor 23 is reversed. The carrier 21 is driven from right to left until the actuator of the left limit switch 28 is depressed, whereupon the drive motor stops. The stage stops in its home position.

FIG. 4 shows the sample holder 12 which provides mechanical sample plate alignment. The sample plates shown in U.S. Pat. Nos. 3,479,265 and 3,635,808 are particularly suitable for use. The substrate of the plate has divisions between sample tracks and is completely dimensionally controlled for size and sample track locations. The sample plate 28 shown in FIG. 4 has eight sample tracks. The sample plate is inserted under the hinged hold-down cover 29. Hold-down cover 29 holds the sample plate against three locating pins 30, 31 and 32. This provides a three point reference which dimensionally locates the sample plate with respect to the sample holder 12 by two of its edges. This allows complete alignment, thereby obviating time-consuming visual alignment. This also eliminates alignment error and inaccurate results in quantification.

Sample holder 12 provides detented movement in the direction of the arrow 33. Detents on bar 34 engage notches such as 35 and 36 in the tracks of the sample stage. The sample holder 12 can be indexed to any one of the eight track positions indicated by the numerals 1 through 8.

With complete alignment assured for the sample tracks, it is possible to mechanically switch from track to track with the detenting movement on the stage. Because the iso-enzyme substrate is dimensionally controlled, this switching from track to track requires no further alignment, thus allowing the machine operator to rapidly and accurately switch from sample track to sample track without touching or realigning the substrate.

The recorder pen mechanism is shown in FIG. 5. The pen 14 is mounted on a pen assembly including cartridge 37 which slides along a traveler bar 38 which is affixed at either end to the sample stage 13. Movement along this bar is orthogonal to the scanning motion of stage 13. Movement along the bar 38 is controlled by a servomechanism which includes servomotor 39 driving capstan pulley 40. The servo potentiometer 41 also has a pulley 42. Pulleys 43-47 are interconnected by cable 48. A carrier 49 and spring 49a maintain tension in the cable 48. Clip 50 secures the pen assembly to the cable 48.

An adjustment plate 51 sets the tension in the cable. It is adjusted and then secured down. The cable is strung with the calibration plate 51 positioned to its limit toward the servomotor 39. Two complete turns are made around the capstan 40. A suitable scale is then attached to the tensioning plate 51 and an appropriate force applied. The tensioning plate initially moves in the direction of pull until the pulling force is balanced by the tensioning spring 49. The calibration plate is then locked in position and the pulling force removed. The proper cable tension to prevent slippage on the servo capstan 40 is thus set. The location of the pen 14 is then set with respect to the potentiometer pulley.

When the sample stage returns to the home position, the cartridge 37 slides under the wedge on the lift cam mechanism 52. Rotation of cartridge 37 about a horizontal axis lifts the pen from the surface of the chart 15.

Figure 6:
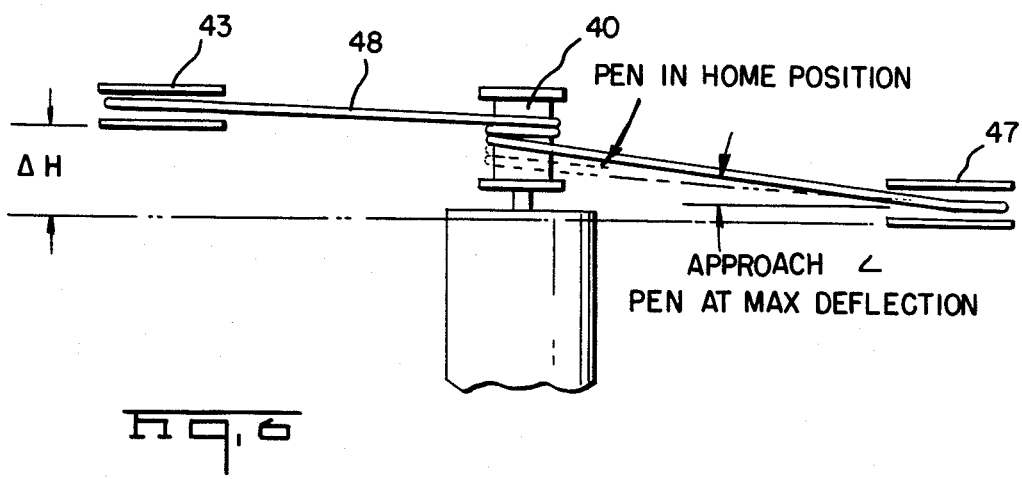
FIG. 6 shows the details of the pen, capstan and cable.

The relationship between capstan and cable illustrated in FIG. 6 is important. To prevent scrubbing of the cable 48 upon itself as the capstan 40 rotates, it is necessary to mount the adjacent pulleys 43 and 47 at different heights ($\Delta H$) to produce the proper approach angle. In addition, sufficient capstan length must be provided to allow for the migration of the wrap cluster as the servomotor rotates both clockwise and counterclockwise. The approach angle is determined by the diameter of the cable, capstan, and the number of turns the capstan must make. $\Delta H$ is determined by all of the above plus the distance each pulley is from the capstan. Mechanically, rotation in either direction of the servomotor causes movement of the tensioned cable and the other elements fixed to it. Since the potentiometer pulley 42 and the pen cartridge 37 are fixed to it, the integrity of the servo system is maintained. Slippage between the servo capstan 40 and the cable 48, should it occur, does not affect the sense of the system as potentiometer position is the sole nulling means. The uncertainty between potentiometer position and pen location is exceedingly low since no gear system with its inherent clearance is involved in their connection, hence dead band and friction is reduced.

While a particular embodiment of the invention has been shown and described, various modifications are within the true spirit and scope of the invention. The appended claims are intended to cover all such modifications.

What is claimed is:

1. An analyzer for fluorescing or absorbing samples comprising:
   a fixedly mounted source of analysis energy;
   a sample stage having a sample holder, a transport mechanism for linearly moving said sample stage with respect to said source to scan said sample across said source;

detection means for generating an electrical signal representing the fluorescence or absorption characteristics of said sample as it is scanned across said source, said detection means being fixed with respect to said source;

a recorder pen mounted on said stage and moved along a chart by the same movement which scans said sample across said source, said recorder pen being driven by said electrical signal in a direction orthogonal to the direction of said movement to produce a record of the fluorescence or absorption characteristics across said sample, said record having the same length as the length of the sample which is scanned.

2. The analyzer recited in claim 1 wherein said transport mechanism further comprises:

a motor for driving said mechanism; and limit switches at both ends of the travel of said mechanism for stopping said motor when said mechanism reaches either extreme of its travel motion.

3. The analyzer recited in claim 1 wherein said recorder pen includes a cartridge rotatable about a horizontal axis;

a lift cam mounted at one end of the movement of said sample stage, said cartridge engaging said lift cam so that rotation thereof lifts said pen out of engagement with said record.

4. The analyzer recited in claim 3 further comprising:

a bar extending orthogonally to the direction of movement of said sample stage, said cartridge being slidable along said bar and rotatable about said bar.

5. The analyzer recited in claim 4 further comprising:

a servomotor driven by the output of said detection means; and a pulley mechanism driven by said servomotor and connected to said cartridge to move it along said bar.

6. An analyzer for fluorescing or absorbing samples comprising:

a source of analysis energy;

a sample stage having a sample holder, said sample stage being linearly movable with respect to said source to scan said sample across said source;

detection means for generating an electrical signal representing the fluorescence or absorption characteristics of said sample as it is scanned across said source;

a recorder pen mounted on said stage and moved along a chart by the same movement which scans said sample across said source, said recorder pen being driven by said electrical signal in a direction orthogonal to the direction of said movement to produce a record of the fluorescence or absorption characteristics across said sample, said record having the same length as the length of the sample which is scanned; and a transport mechanism for linearly moving said sample stage including:

a way rod which is fixedly mounted;

a carrier affixed to said sample stage and slidable along said way rod;

a motor for driving said mechanism;

a pulley driven by said motor;

a cable attached at both ends to said carrier, said cable being wrapped around said pulley so that rotation of said pulley is translated to said linear movement of said carrier; and limit switches at both ends of the travel of said mechanism for stopping said motor when said mechanism reaches either extreme of its travel motion.

7. An analyzer for fluorescing or absorbing samples having a plurality of sample tracks comprising:

a source of analysis energy;

a sample stage, said sample stage being linearly movable with respect to said source to scan said sample across said source;

a sample holder mounted on said sample stage, said sample holder being movable with respect to said sample stage in a direction orthogonal to the direction of movement of said sample stage so that different sample tracks are scanned;

detection means for generating an electrical signal representing the fluorescence or absorption characteristics of said sample as it is scanned across said source;

a recorder pen mounted on said stage and moved along a chart by the same movement which scans said sample across said source, said recorder pen being driven by said electrical signal in a direction orthogonal to the direction of said movement to produce a record of the fluorescence or absorption characteristics across said sample, said record having the same length as the length of the sample which is scanned.

8. The analyzer recited in claim 7 further comprising:

a case enclosing said source and said optical detection means;

said sample holder for said record being on the outside of said case, said sample holder being movable with respect to said sample stage in a direction orthogonal to the direction of movement of said sample stage so that a sample can be inserted in said sample holder which is moved inside said case into proximity with said source and said optical detection means.

9. The analyzer recited in claim 8 wherein said sample holder has a detent which engages said sample stage at positions in the movement of said sample holder with respect to said stage to provide different scanning tracks across said sample.

10. The analyzer recited in claim 9 further comprising:

locating pins on said sample holder for accurately aligning said sample with respect to said holder.

11. The analyzer recited in claim 10 further comprising:

a hinged hold-down cover for holding said sample with respect to said locating pins.

* * * * *